(12) United States Patent
Blank et al.

(10) Patent No.: US 8,461,836 B2
(45) Date of Patent: Jun. 11, 2013

(54) METHOD AND DEVICE FOR EX SITU MAGNETIC RESONANCE ANALYSIS

(75) Inventors: Aharon Blank, Kfar-Vradim (IL); Itai Katz, Nofit (IL)

(73) Assignee: Technion Research & Development Foundation Limited, Haifa (IL)

( * ) Notice: Subject to any disclaimer, the term of this patent is extended or adjusted under 35 U.S.C. 154(b) by 429 days.

(21) Appl. No.: 12/675,801

(22) PCT Filed: Aug. 27, 2008

(86) PCT No.: PCT/IL2008/001164
§ 371 (c)(1),
(2), (4) Date: Mar. 1, 2010

(87) PCT Pub. No.: WO2009/027973
PCT Pub. Date: Mar. 5, 2009

(65) Prior Publication Data
US 2010/0308820 A1    Dec. 9, 2010

Related U.S. Application Data

(60) Provisional application No. 60/935,789, filed on Aug. 30, 2007.

(51) Int. Cl.
*G01V 3/00* (2006.01)
(52) U.S. Cl.
USPC .......................................................... 324/303
(58) Field of Classification Search
USPC .................................. 324/300–322
See application file for complete search history.

(56) References Cited

U.S. PATENT DOCUMENTS

| 4,717,876 | A | 1/1988 | Masi et al. |
| 5,757,186 | A * | 5/1998 | Taicher et al. ................. 324/303 |
| 6,111,409 | A * | 8/2000 | Edwards et al. .............. 324/303 |
| 6,121,773 | A * | 9/2000 | Taicher et al. ................. 324/303 |
| 6,489,872 | B1 | 12/2002 | Fukushima et al. |
| 7,095,230 | B2 | 8/2006 | Blumich et al. |
| 7,368,909 | B2 * | 5/2008 | Blanz et al. ................... 324/303 |
| 7,528,600 | B2 * | 5/2009 | Sen et al. ....................... 324/303 |
| 7,808,238 | B2 * | 10/2010 | Chen ............................... 324/303 |
| 2003/0052677 | A1 | 3/2003 | Pines et al. |

FOREIGN PATENT DOCUMENTS

| EP | 0512345 | 11/1992 |
| EP | 0795757 | 9/1997 |
| JP | 05-049614 | 3/1993 |
| WO | WO 99/54747 | 10/1999 |
| WO | WO 2006/010955 | 2/2006 |
| WO | WO 2009/027973 | 3/2009 |

OTHER PUBLICATIONS

International Search Report and the Written Opinion Dated Jun. 27, 2009 From the International Searching Authority Re.: Application No. PCT/IL2008/001164.

(Continued)

*Primary Examiner* — Dixomara Vargas

(57) ABSTRACT

A device for ex situ magnetic resonance analysis is disclosed. The device comprises a static magnetic field unit (12) for generating a generally cylindrically symmetric static magnetic field outside the static magnetic field unit, and a radiofrequency unit (14) for generating a generally cylindrically symmetric radiofrequency field outside the radiofrequency unit. The radiofrequency field is perpendicular to the static magnetic field. A spatial inhomogeneity of the magnetic field substantially matches a spatial inhomogeneity of the radiofrequency field.

25 Claims, 7 Drawing Sheets

OTHER PUBLICATIONS

International Preliminary Report on Patentability Dated Mar. 11, 2010 From the International Bureau of WIPO Re.: Application No. PCT/IL2008/001164.

International Search Report Dated Jan. 27, 2009 From the International Searching Authority Re.: Application No. PCT/IL2008/001164.

Written Opinion Dated Jan. 27, 2009 From the International Searching Authority Re.: Application No. PCT/IL2008/001164.

Manz et al. "A Mobile One-Sided NMR Sensor With a Homogeneous Magnetic Field: The NMR-MOLE", Journal of Magnetic Resonance, XP005723717, 183(1): 25-31, Nov. 7, 2006. Chap.3, Fig. 1.

* cited by examiner

METHOD AND DEVICE FOR EX SITU MAGNETIC RESONANCE ANALYSIS

RELATED APPLICATIONS

This Application is a National Phase of PCT Patent Application No. PCT/IL2008/001164 having International filing date of Aug. 27, 2008, which claims the benefit of U.S. Provisional Patent Application No. 60/935,789 filed on Aug. 30, 2007. The contents of the above Applications are all incorporated herein by reference.

FIELD AND BACKGROUND OF THE INVENTION

The present invention, in some embodiments thereof, relates to magnetic resonance and, more particularly, but not exclusively, to an ex-situ magnetic resonance probe.

Nuclear Magnetic Resonance (NMR) is a quantum mechanical phenomenon in which a system of spins placed in a static magnetic field resonantly absorbs energy when applied with a certain electromagnetic frequency. This phenomenon is exploited in many applications, such as spectroscopy and Magnetic Resonance Imaging (MRI), for obtaining information regarding the chemical and physical microscopic properties of materials.

A nucleus can experience NMR only if its nuclear spin I does not vanish, i.e., the nucleus has at least one unpaired nucleon. Examples of non-zero spin nuclei frequently used in MRI include $^1H$ (I=½), $^2H$ (I=1), $^{23}Na$ (I=3/2), etc. When placed in a magnetic field, a nucleus having a spin I is allowed to be in a discrete set of energy levels, the number of which is determined by I, and the separation of which is determined by the gyromagnetic ratio of the nucleus and by the magnetic field. Under the influence of a small perturbation, manifested as a radiofrequency magnetic field (commonly referred to as $B_1$, which rotates about the direction of a primary static magnetic field (commonly referred to as $B_0$), the nucleus has a time dependent probability to experience a transition from one energy level to another. With a specific frequency of the rotating magnetic field, the transition probability may reach the value of unity. Hence at certain times, a transition is forced on the nucleus, even though the rotating magnetic field may be of small magnitude relative to the primary magnetic field. For an ensemble of spin nuclei the transitions are realized through a change in the overall magnetization.

Once a change in the magnetization occurs, a system of spins tends to restore its magnetization longitudinal equilibrium value, by the thermodynamic principle of minimal energy. The time constant which control the elapsed time for the system to return to the equilibrium value is called "spin-lattice relaxation time" or "longitudinal relaxation time" and is denoted $T_1$. An additional time constant, $T_2$ ($\leq T_1$), called "spin-spin relaxation time" or "transverse relaxation time", controls the elapsed time in which the transverse magnetization diminishes, by the principle of maximal entropy. However, inter-molecule interactions and local variations in the value of the static magnetic field, may alter the "intrinsic" value of $T_2$, to an actual observed value denoted $T_2^*$.

In conventional NMR spectroscopy or MRI systems, the sample to be investigated is placed in the bore of a static magnet. Whilst the conventional approach is generally preferable in terms of cost effective generation of the strong and uniform static magnetic field required for NMR measurements, the particular circumstances of some applications demand measurements which can only be achieved with a remotely-positioned instrument (commonly termed "ex-situ" NMR).

In recent years ex-situ NMR has become an increasingly important measurement technique in many applications, particularly oil well logging, and material research applications. Ex-situ NMR is different from conventional NMR spectroscopy and imaging insofar as the investigated sample is outside the apparatus. Therefore the static and rotating fields are typically far from being homogeneous. From the point of view of the measurement the sample may be infinite in size but the volume which contributes useful signal is limited.

Ex-situ NMR is also referred to in the literature as: "inside-out NMR", "external field NMR", "remotely positioned MR", "projected field MR" and "one-sided MR".

U.S. Pat. No. 7,358,734 discloses a sensor for ex situ magnetic resonance profiling with microscopic resolution. The sensor includes a magnet system with two pairs of permanent magnet blocks which are oppositely polarized for producing a magnetic field constant in a plane external to the body. A radiofrequency circuit is placed between the pairs.

Perlo et al. [Science, Vol. 315, No. 5815, pp. 1110-1112 (published online Jan. 10, 2007)] disclose a technique in which a variety of permanent magnet blocks, as well as "shim coils" are employed to homogenize the magnetic field just outside the probe.

Another technique, [Perlo et al., Journal of Magnetic Resonance 180 (2006) 274; Perlo et al., Science, 308 (2005) 1279] uses a similar portable nuclear magnetic resonance sensor with a single-sided open probe design. The probe includes a U-shaped main magnet, an inner magnet and a rectangular surface radiofrequency coil. The dimensions of the coil and the position of the inner magnet are adjusted to optimize the correspondence between the static and radiofrequency magnetic fields so that their spatial dependence has the same functional description (up to a constant). The resulting magnetic field inhomogeneity is compensated by a special pulse sequence that takes advantage this identical functional and results in an NMR signal called "nutation echo". This probe can acquire fluorine-19 spectra of liquid fluorocarbons with 8 parts per million (ppm) resolution.

Additional background art includes Meriles et al., Science 293 No. 5527, 82-85 (2001); Eidmann et al., Journal of Magnetic Resonance A 122 (1996) 104; and Blank et al., Magnetic Resonance in Medicine, 54 (2005) 105.

SUMMARY OF THE INVENTION

According to an aspect of some embodiments of the present invention there is provided a device for ex situ magnetic resonance analysis. The device comprises: a static magnetic field unit for generating a generally cylindrically symmetric static magnetic field outside the static magnetic field unit; and a radiofrequency unit for generating a generally cylindrically symmetric radiofrequency field outside the radiofrequency unit. The radiofrequency field is perpendicular to the static magnetic field. In various exemplary embodiments of the invention the cylindrical symmetries are with respect to the same symmetry axis. In various exemplary embodiments of the invention a spatial inhomogeneity of the magnetic field substantially matches a spatial inhomogeneity of the radiofrequency field.

According to an aspect of some embodiments of the present invention there is provided a method of performing ex situ magnetic resonance analysis. The method comprises: subjecting a sample to a generally cylindrically symmetric magnetic field generated outside a static magnetic field unit, applying to the sample a generally cylindrically symmetric radiofrequency field, and acquiring nuclear magnetic resonance data from the sample, thereby performing ex situ magnetic resonance analysis.

According to some embodiments of the invention the acquisition of the nuclear magnetic resonance data comprises employing a nutation echo sequence.

According to some embodiments of the present invention the device and/or method is capable of providing nuclear magnetic resonance data at a spectral resolution of less than 8 ppm over an effective volume of at least 3 cubic millimeters being at a distance of at least 2 mm from an end of the static magnetic field unit.

According to some embodiments of the present invention the device and/or method is capable of providing nuclear magnetic resonance data at a spectral resolution of less than 3 ppm over an effective volume of at least 2 cubic millimeters being at a distance of at least 2 mm from an end of the static magnetic field unit.

According to some embodiments of the present invention the device and/or method is capable of providing nuclear magnetic resonance data at a spectral resolution of less than 8 ppm over an effective volume of at least 2 cubic millimeters being at a distance of at least 10 millimeters from the static magnetic field unit.

According to some embodiments of the present invention the device and/or method is capable of providing nuclear magnetic resonance data at a spectral resolution of less than 8 ppm and a signal-to-noise ratio of at least 30 for an acquisition time of about 1 min over an effective volume which is at least 2 cubic millimeters being at a distance of at least 2 millimeters from the static magnetic field unit.

According to some embodiments of the present invention the device and/or method is capable of providing nuclear magnetic resonance data at a spectral resolution of less than 3 ppm and a signal-to-noise ratio of at least 30 for an acquisition time of about 1 min over an effective volume which is at least 3 cubic millimeters being at a distance of at least 10 millimeters from the static magnetic field unit.

According to some embodiments of the present invention the static magnetic field unit comprises a permanent magnet.

According to some embodiments of the present invention the static magnetic field unit comprises a superconductor magnet assembly.

According to some embodiments of the present invention the device and/or method is capable of providing nuclear magnetic resonance data at a spectral resolution of less than 2 ppm over an effective volume of at least 500 cubic millimeters being at a distance of at least 20 mm from an end of the static magnetic field unit.

According to some embodiments of the present invention the device and/or method is capable of providing nuclear magnetic resonance data at a spectral resolution of less than 1 ppm over an effective volume of at least 10 cubic millimeters being at a distance of at least 20 mm from an end of the static magnetic field unit.

According to some embodiments of the present invention the device and/or method is capable of providing nuclear magnetic resonance data at a spectral resolution of less than 2 ppm over an effective volume of at least 10 cubic millimeters being at a distance of at least 50 millimeters from the static magnetic field unit.

According to some embodiments of the present invention the device and/or method is capable of providing nuclear magnetic resonance data at a spectral resolution of less than 2 ppm and a signal-to-noise ratio of at least 50,000 for an acquisition time of about 1 min over an effective volume which is at least 10 cubic millimeters being at a distance of at least 20 millimeters from the static magnetic field unit.

According to some embodiments of the present invention the device and/or method is capable of providing nuclear magnetic resonance data at a spectral resolution of less than 1 ppm and a signal-to-noise ratio of at least 50,000 for an acquisition time of about 1 min over an effective volume which is at least 50 cubic millimeters being at a distance of at least 50 millimeters from the static magnetic field unit.

According to some embodiments of the invention the radiofrequency unit comprises a set of radiofrequency coils arranged about the symmetry axis.

According to some embodiments of the invention the radiofrequency unit comprises at least two sets of radiofrequency coils, and wherein different sets of radiofrequency coils are configured for different types of excitation pulses.

According to some embodiments of the invention the application of the radiofrequency field comprises applying different types of excitation pulses using different sets of radiofrequency coils.

According to some embodiments of the invention the device further comprises a plurality of shim coils for correcting a profile of the static magnetic field.

According to some embodiments of the invention the method further comprises applying correcting a profile of the static magnetic field using a plurality of shim coils.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
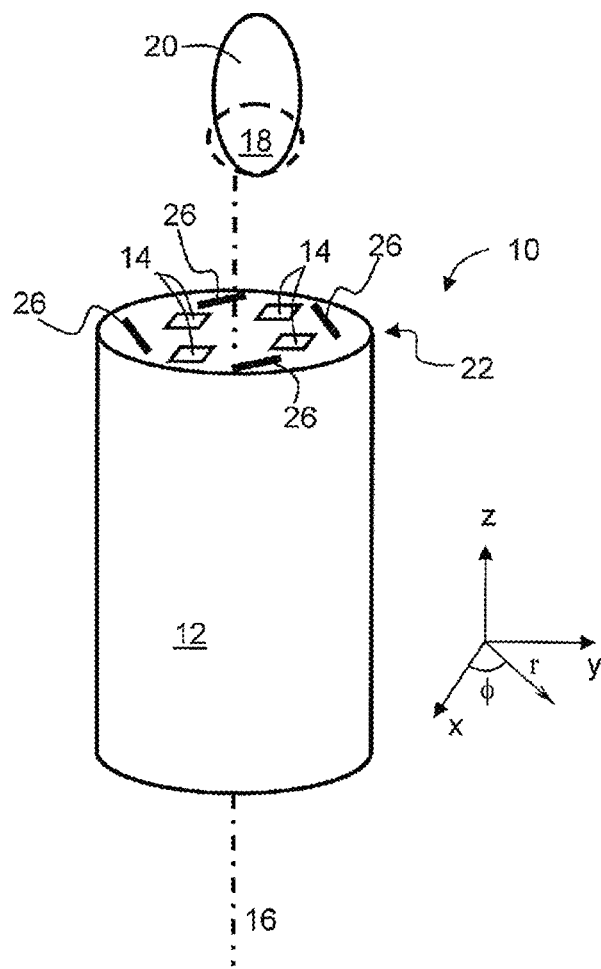
Figure 1B:
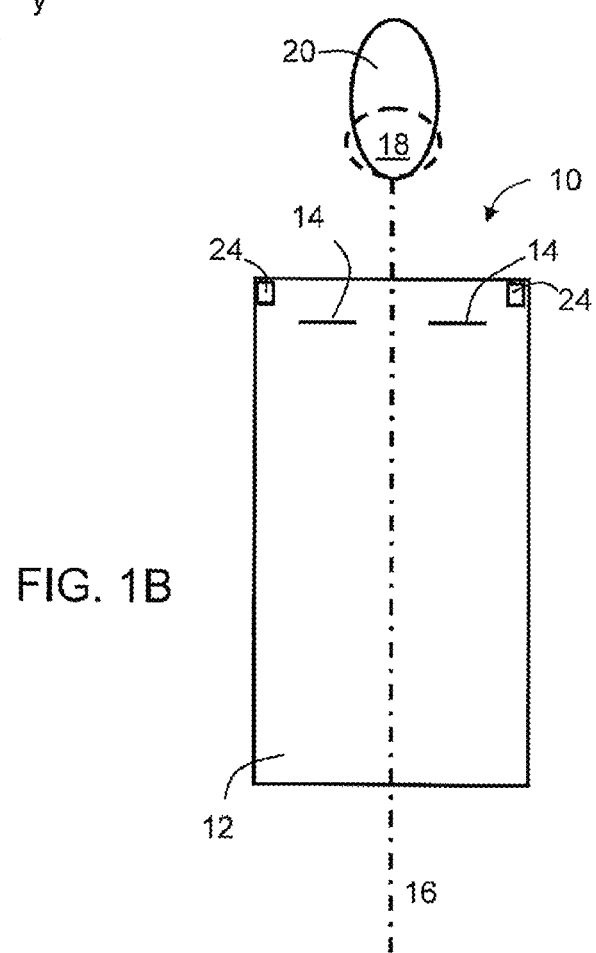
Figure 2A:
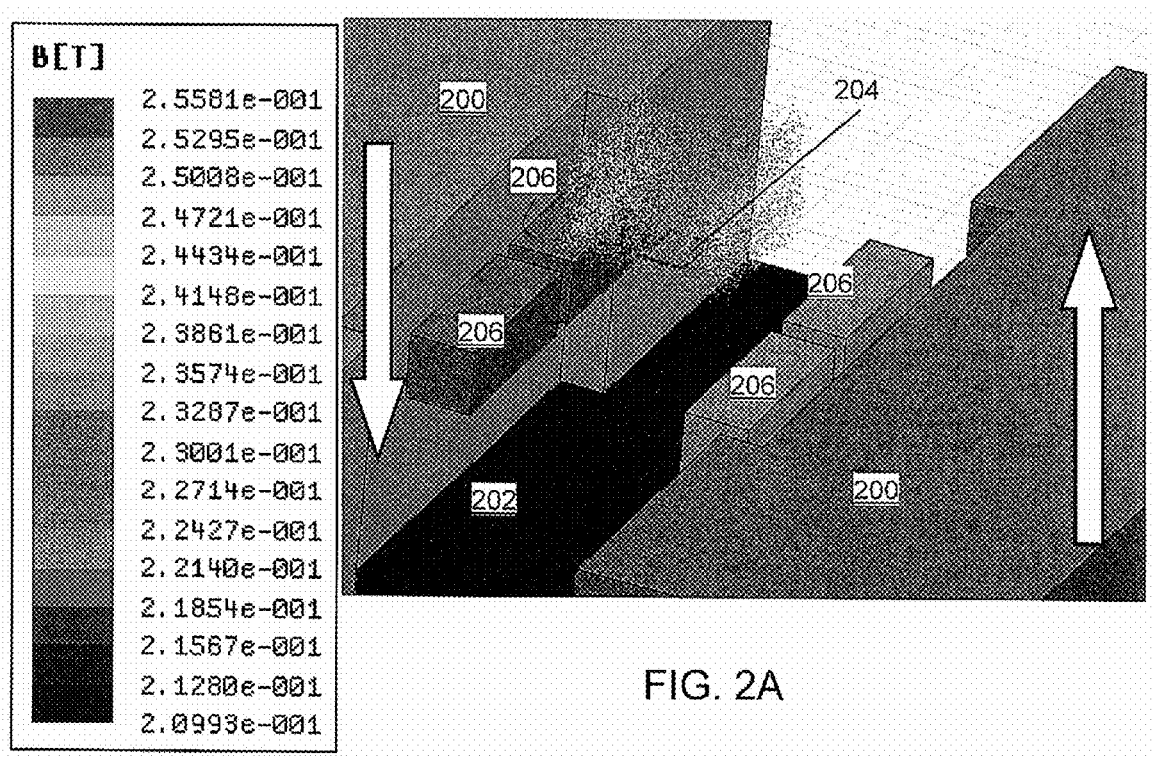
Figure 2B:
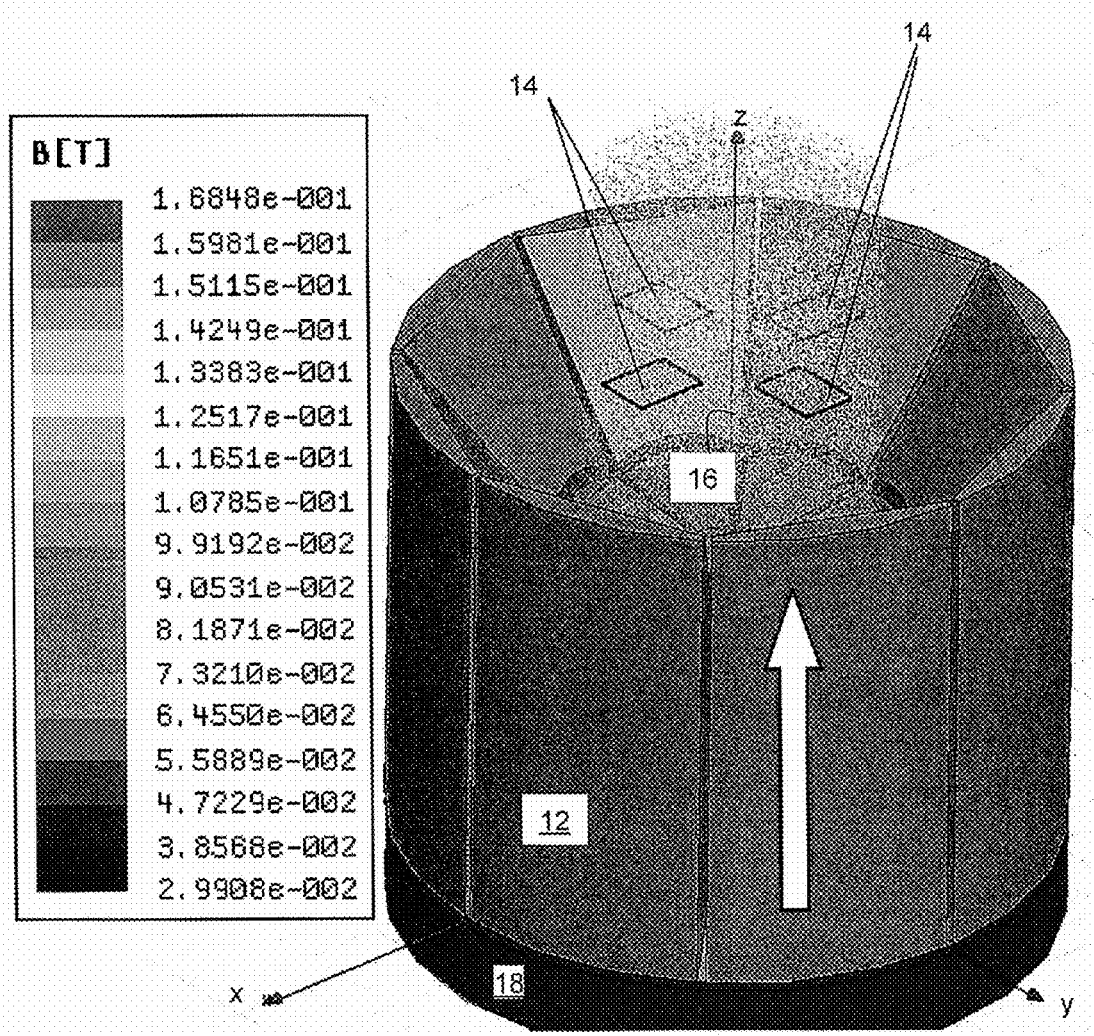
Figure 4A:
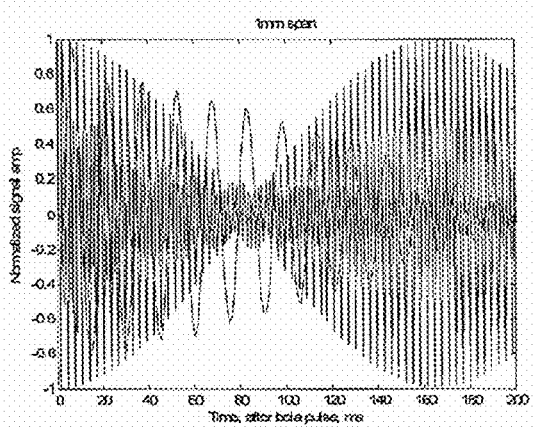
Figure 4B:
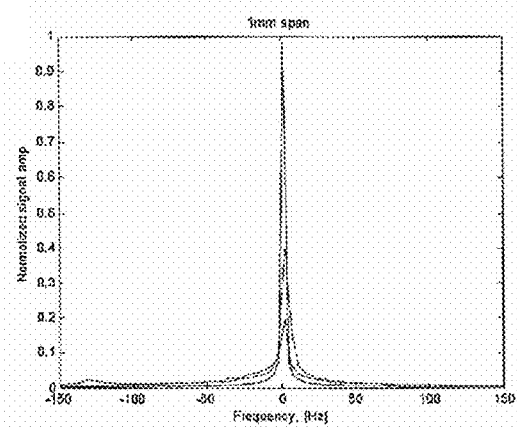
Figure 5:
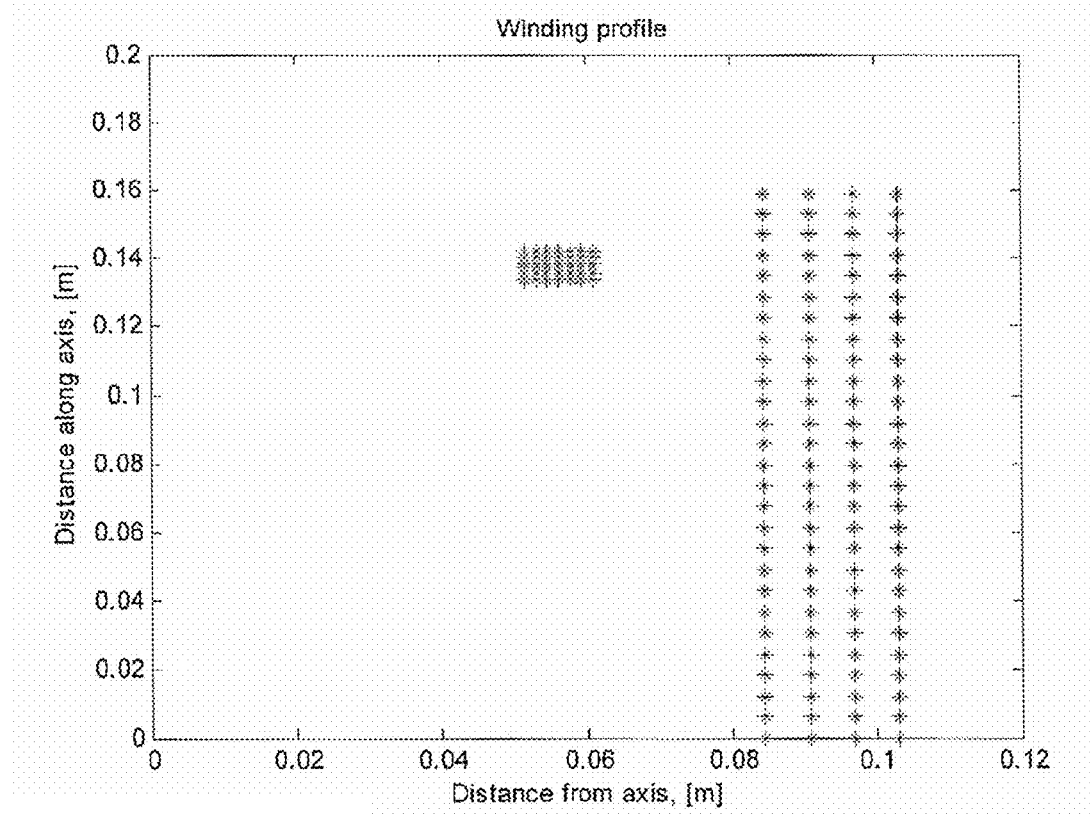
Figure 6:
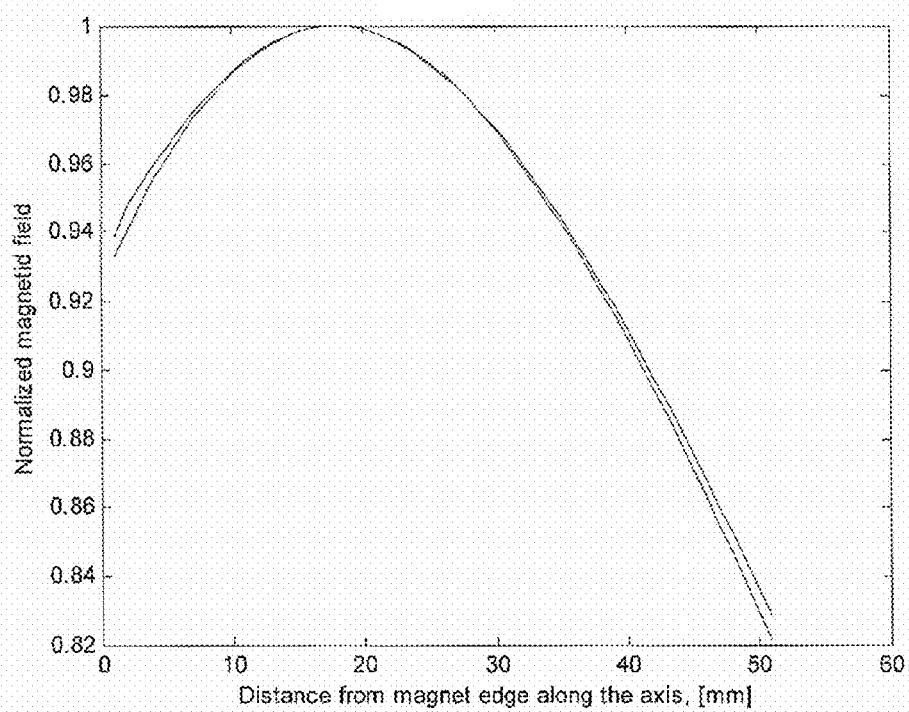
Figure 7A:
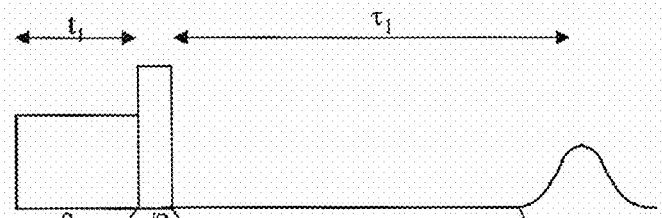
Figure 7B:
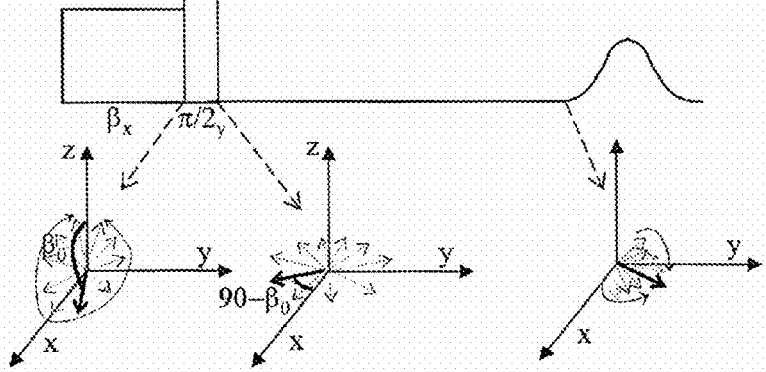

FIGS. 1A-B are schematic illustrations of a perspective view (FIG. 1A) and a cross sectional view (FIG. 1B) of a probe device for ex situ magnetic resonance analysis, according to various exemplary embodiments of the present invention;

FIGS. 2A-B are schematic illustrations of two probe device configuration used in computer simulations performed according to various exemplary embodiments of the present invention;

FIGS. 3A-F show the static and RF magnetic fields of the configurations illustrated in FIGS. 2A-B, plotted as a function of the distance from the edge of the magnet;

FIG. 4A shows the real part of a nutation echo signal as a function of the time after the β pulse for the configurations illustrated in FIGS. 2A-B;

FIG. 4B shows the Fourier transform of the time domain signals shown in FIG. 4A;

FIGS. 4C-H show NMR spectra simulations for the configurations illustrated in FIGS. 2A-B;

FIG. 5 is a schematic illustration of a winding profile for a cylindrically symmetric superconductor magnet, according to various exemplary embodiments of the present invention;

FIG. 6 shows static magnetic fields produced by a superconductor magnet and a permanent magnet, according to various exemplary embodiments of the present invention;

FIG. 7A is a schematic illustration of a nutation echo pulse sequence which can be used according to various exemplary embodiments of the present invention; and FIG. 7B is a schematic illustration of respective magnetizations resulting from the pulses of FIG. 7A.

DESCRIPTION OF SPECIFIC EMBODIMENTS OF THE INVENTION

The present invention, in some embodiments thereof, relates to magnetic resonance and, more particularly, but not exclusively, to an ex-situ magnetic resonance probe.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Due to the inhomogeneity of the static magnetic field outside a magnetic resonance system, traditional ex-situ probes are useful only for characterizing a sample by means of its NMR relaxation times $T_1$ and $T_2$ and/or the diffusion coefficient D of the protons in the sample which, can be extracted from the $T_2$ information and the gradient of the static magnetic field. However, $T_1$, $T_2$ and D mainly characterize the physical nature of a sample while oftentimes it is desired also to identify the chemical composition of the sample.

Thus, according to an aspect of some embodiments of the present invention there is provided a probe device for ex situ magnetic resonance analysis, generally referred to herein as device 10.

Referring now to the drawings, FIGS. 1A-B illustrate a perspective view (FIG. 1A) and a cross sectional view (FIG. 1B) of probe device 10, according to various exemplary embodiments of the present invention. Device 10 can be used for performing magnetic resonance analysis (e.g., NMR spectroscopy, magnetic resonance imaging) of a sample 20 placed outside device 10 and adjacent thereto.

Device 10 comprises a static magnetic field unit 12 which generates a generally cylindrically symmetric magnetic field outside unit 12, and a radiofrequency unit 14 which generates a generally cylindrically symmetric radiofrequency field outside unit 14. Both fields extend away from device 10 sufficiently to penetrate sample 20 or at least a region-of-interest within sample 20. The direction of the static field is generally along the z direction and the direction of the radiofrequency is generally perpendicular to the z direction (i.e., parallel to the x-y plane) as known to those skilled in the art of NMR.

As used herein, "generally cylindrically symmetric" means that there are no or low variations in the respective field as a function of an azimuthal angle ϕ measured perpendicular to a symmetry axis 16. The variations of a generally cylindrically symmetric field along any circle whose center is on the symmetry axis and which engages a plane perpendicular to the symmetry axis are preferably lower than 100 ppm, more preferably lower than 10 ppm, more preferably lower than 1 ppm.

Since a cylindrical symmetry is employed, some of the following description is formulated in terms of a cylindrical coordinate system (z, r, ϕ), where z is referred to as the longitudinal coordinate, r is referred to as the radial coordinate and ϕ is referred to as the azimuthal coordinate. The relations between a Cartesian and cylindrical coordinate systems are known in the art and are illustrated in FIG. 1A.

In various exemplary embodiments of the invention the units 12 and 14 are aligned such that the cylindrical symmetries of the two fields are with respect to the same symmetry axis 16, which is along the z direction.

Since sample 20 is placed outside device 10, the static magnetic field is inhomogenous. In various exemplary embodiments of the invention the inhomogeneity of the static magnetic field substantially matches (e.g., within 10% or less) the inhomogeneity of the radiofrequency field.

Ideally, the matching can be formulated mathematically as the following relation between the derivatives of the magnetic fields $B_0$ and $B_1$:

$$\frac{dB_0(r)}{dx_i} = \kappa \frac{dB_1(r)}{dx_i}, \tag{1}$$

where $x_i$, represents 3 orthogonal axes in 3D, r=(z, r, ϕ) is the displacement vector in cylindrical coordinates and κ is a numerical constant that does not depend or has a weak dependence (e.g., less than a few tens of ppm, more preferably less than 10 ppm over a range of a few millimeters) on r.

Preferably, this matching extends over a longitudinal distance (as measured along the z coordinate from the end 22 of device 10 which is proximal to sample 20) and transverse distance (as measured along the r coordinate from axis 16) of at least 2 millimeters, more preferably at least 3 millimeters, more preferably at least 5 millimeters, more preferably at least 8 millimeters, more preferably at least 10 millimeters.

Static magnetic field unit 12 can comprise a permanent magnet, which can have the shape of a cylinder or any other shape that generates cylindrically symmetric magnetic field. In various exemplary embodiments of the invention device 10 comprises a single permanent magnet (such as powerful rare earth magnet based on sintered NdFeB). Unit 12 can also comprise a superconductor magnet assembly. For example, a reciprocal winding profile (see, e.g., FIG. 5 in the Examples section that follows) that produces a cylindrically symmetric static magnetic field. The advantage of a superconductor for unit 12 is that such configuration can generate higher magnetic fields (about 5T or more, compared to a 0.1-0.2 T of a permanent magnet configuration) and thus improve the characteristics of probe device 10. The superconductor magnet assembly can be based on cryogenic cooling, for example, liquid helium of or a closed cycle cooler (so called cryogen free superconductor).

Radiofrequency unit 14 can be configured to produce any pulse sequence suitable for NMR spectroscopy or MRI. In some embodiments of the present invention unit 14 is configured to provide a nutation echo pulse sequence such as the pulse sequence illustrated in FIG. 7A.

In the embodiments illustrated in FIG. 7A, a $\beta_x$ pulse which rotates spins located at r=0 to at an angle $\beta_0$ from the z direction. The duration of the $\beta_x$ pulse is denoted $t_1$ in FIG. 7A. The $\beta_x$ pulse is immediately followed by a $\pi/2_y$ pulse which rotates the magnetization by 90° and produces a magnetization at an angle of 90°−$\beta_0$ to the x direction. Following a free evolution period of $\tau_1$ ms, unit 14 can produce an acquisition pulse sequence. The respective magnetizations resulting from the pulses of FIG. 7A are illustrated in FIG. 7B. A typical value for $t_1$ is from about 0.1 ms to about 200 ms, and a typical value for $\tau_1$ is from about 1 ms to about 1000 ms.

In some embodiments of the present invention radiofrequency unit 14 comprises a set of radiofrequency coils arranged about symmetry axis 16. Shown in FIG. 1 are four radiofrequency coils arranged about symmetry axis 16, but this need not necessarily be the case, since in some embodiments, a different number of radiofrequency coils can be employed. The coils can be used both for generating radiofrequency excitation pulses and for signal acquisition. In some embodiments one coil or one set of coils is used for generating the radiofrequency field and another coil or set of coils can be used for reception. Signal reception does not have to exhibit spatial matching with the static field. Unit 14 can comprise more than one set of radiofrequency coils to generate cylindrical symmetric and spatially matched radiofrequency field. This embodiment is particularly useful when it is desired to design the coils for particular excitation pulses. Thus, different sets of radiofrequency coils can be configured for different types of excitation pulses. In some embodiments of the present invention one or more sets of radiofrequency coils are designated for signal acquisition, while other sets are designated for generating the excitation pulses. For example, three sets of coils can be employed, where a first set is used for a β radiofrequency pulse, a second set is used for a 90° radiofrequency pulse and a 180° radiofrequency pulse, and a third set can be used for signal acquisition (see for example, the nutation echo pulse sequence shown in FIG. 7). The cylindrical symmetry employed by the present embodiments facilitates a probe design with only two independent axes (unlike conventional configurations in which there is no such symmetry and there are field variations along three independent axes). This can lead to a better spatial matching of the fields. The ability to use a superconductor magnet assembly also improves the performances of the probe device since higher strength of the static field results in higher spectral resolution.

It was found by the inventors of the present invention that the probe device of the present embodiments exhibits improved properties over conventional devices in at least one of: spectral resolution, size of the effective volume, signal-to-noise ratio and distance from the effective volume to device. Techniques for designing the static magnetic field unit and the radiofrequency unit in accordance with some embodiments of the present invention are provided in the examples section that follows.

In some embodiments of the present invention device 10 is capable of providing NMR data at a spectral resolution of less than 8 ppm, more preferably less than 6 ppm, more preferably less than 4 ppm, more preferably less than 3 ppm, more preferably less than 2 ppm, e.g., about 1 ppm or less over a predetermined effective volume 18 outside the probe device. Effective volume 18 is marked by a dash line in FIGS. 1A and 1B. Sample 20 can engage part or the entire effective volume 18.

In some embodiments of the present invention the predetermined effective volume is of at least 2 $mm^3$, more preferably at least 3 $mm^3$, more preferably at least 4 $mm^3$, more preferably at least 5 $mm^3$, more preferably at least 6 $mm^3$, more preferably at least 7 $mm^3$, e.g., about 9 $mm^3$ or more.

When a superconductor magnet assembly is employed, the predetermined effective volume is of at least 20 $mm^3$, more preferably at least 100 $mm^3$, more preferably at least 500 $mm^3$, e.g., about 1000 $mm^3$ or more.

The above typical effective volumes are typical for a probe device having a static magnetic field unit of about 160 mm in diameter and about 120 mm in height. For other sizes of the static magnetic field unit, the typical effective volumes are cubically scaled. Specifically, when the diameter and height of the static magnetic field unit is changed by a factor of X, the above typical effective volumes are changed by a factor of $X^3$.

In some embodiments of the present invention the predetermined effective volume is at a distance along the z direction of at least 2 mm, more preferably at least 4 mm, more preferably at least 6 mm, e.g., about 8 mm or more from the surface of the device.

When a superconductor magnet assembly is employed, the predetermined effective volume is at a distance along the z direction of at least 20 mm, more preferably at least 40 mm, more preferably at least 50 mm, e.g., about 100 $mm^3$ or more.

The above distances are typical for a probe device having a static magnetic field unit of about 160 mm in diameter and about 120 mm in height. For other sizes of the static magnetic field unit, the typical distances are linearly scaled. Specifically, when the diameter and height of the static magnetic field unit is changed by a factor of X, the above typical distances are changed by the same factor X.

In some embodiments of the present invention the probe device is capable of providing NMR data at a signal-to-noise ratio of at least 10, more preferably at least 20, more preferably at least 30 for an acquisition time of about 1 min.

When a superconductor magnet assembly is employed, the typical signal-to-noise ratio can be at least 50,000 $mm^3$, more preferably at least 100,000 $mm^3$.

The above values of signal-to-noise ratio are typical for a probe device having a static magnetic field unit of about 160 mm in diameter and about 120 mm in height. For other sizes of the static magnetic field unit, the typical signal-to-noise ratios are quadratically scaled. Specifically, when the diameter and height of the static magnetic field unit is changed by a factor of X, the above typical signal-to-noise ratios are changed by a factor of $X^2$.

In some embodiments of the present invention device 10 comprises one or more shim coils 24 for correcting the profile of the static magnetic field which can be located at or below the upper surface of the cylindrical probe (see FIG. 1B). Also contemplated is the use of radiofrequency shim pulses to increase the size of the effective volume. This can be done, for example, using the technique disclosed in Topgaard et al., Proceedings of the National Academy of Sciences of the United States of America, 101 (2004) 17576.

According to an aspect of some embodiments of the present invention there is provided a method of performing ex situ magnetic resonance analysis. The method comprises: subjecting a sample to a generally cylindrically symmetric magnetic field generated outside a static magnetic field unit, applying to the sample a generally cylindrically symmetric radiofrequency field which is perpendicular to the static magnetic field, and acquiring nuclear magnetic resonance data from the sample, thereby performing ex situ magnetic resonance analysis.

In various exemplary embodiments of the invention the cylindrical symmetries are with respect to the same symmetry axis. In various exemplary embodiments of the invention a spatial inhomogeneity of the magnetic field substantially matches a spatial inhomogeneity of the radiofrequency field.

At least part of the method of the present embodiments can be executed by means of the probe device described above.

The probe device and method of the present embodiments can be used in many applications. In some embodiments of the present invention the probe device or method is used in chemically-related applications where spectroscopic NMR measurements are required for samples located outside the magnet. For example, the probe device and method of the present embodiments can be used for performing measurements during chemical reactions and quality inspection of chemicals and common commercial products (e.g., wine, medicine) stored in closed containers without opening the containers. The probe device and method of the present embodiments can also be used for measuring and/or characterizing of rare items.

The probe device and method of the present embodiments can be used in the exploitation of hydrocarbon reservoirs. For example, in some embodiments of the present invention the probe device or method is used as an NMR borehole logging tool for determining the liquid contents of pore volume within a reservoir as described e.g., in U.S. Pat. No. 6,094,048, and/or data (e.g., porosity, clay mineral content) relating to the composition of a geologic structure as described in U.S. Pat. No. 5,557,200. In some embodiments of the present invention the probe device or method is used in the oil industry for determining one or more transport properties (e.g., diffusion coefficients, electrical resistivity factors and permeability to fluid flow) of porous and permeable earth formations as described e.g., in U.S. Pat. No. 4,719,423.

The probe device and method of the present embodiments can be used for determining concrete strength, potential shrinkage and readiness to accept coverings, as described, e.g., in U.S. Pat. No. 5,672,968, the contents of which are hereby incorporated by reference.

The probe device and method of the present embodiments can be used in clinical applications, both for spectroscopy and for imaging. This embodiment is particularly useful when a superconductor magnet assembly is employed form generating the static magnetic field. To this end, the probe device and method of the present embodiments can be used for producing magnetic resonance images of a body of a human or an animal. For example, the present embodiments can be useful for imaging and or analyzing organic and biological molecules, such as, but not limited to, proteins, glycoproteins, proteolipids, lipids, carbohydrates, nucleic acids, and any complex of macromolecules which comprises at least two of the above types of molecules.

Magnetic resonance images can be obtained according to the present embodiments for the whole body of the mammalian subject or for any part (e.g., organ) thereof, including, without limitation, the brain, the heart, a kidney, a gland, a testicle, an ovary, an eye, the liver, the pancreas and the spleen. Such images can provide information regarding the type and/or content of various tissues, such as, but not limited to, tendons, skin portions, bones, muscles, cartilages, blood vessels, ligaments, nerves, lymph nodes and the like.

Also contemplated are embodiment in which the probe device or method is used for analysis purposes, e.g., spectroscopy and the like. In these embodiments, the body can be a sample of a biological material (e.g., a tissue sample, a plant sample) or a non-biological material. The analyzed material can have a water component and optionally one or more molecular species or rigid structures such as membranes.

Magnetic resonance analysis or imaging of biological materials according to the present embodiments can be performed on live human or animals or ex-vivo.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Numerical Simulations

The present examples demonstrate numerical simulations performed in accordance with some embodiments of the present invention for optimal NMR conditions at the location of the effective volume. The effective volume at which the optimal NMR conditions are achieved is interchangeably referred to as the "sweet volume." The purposes of the numerical simulations were to determine the size of the effective volume and the signal-to-noise-ratio.

Effective Volume

The effective volume is the volume in which adequate matching between the static and radiofrequency fields is achieved. It is desirable to have a sufficiently large effective volume which is located sufficiently far from the probe device.

Two ex-situ probe configurations were examined with the purpose of showing the advantages of the cylindrical symmetry employed by some embodiments of the present invention.

A first configuration, referred to as "rectangular", is illustrated in FIG. 2A. This configurations is similar to the configuration disclosed in Perlo et al. 2006 supra, and included a U-shaped magnet with two magnets blocks 200 with opposite polarization placed on an iron yoke 204. The gap between the magnets blocks was 10 cm in the central region and 8 cm at the borders. A shimming unit 206 which included four shim coils produced a field with opposite sign and a gradient comparable to the main field. The direction of the static field is marked by a block arrows in FIG. 2A.

A second probe configuration, referred to as "cylindrical," is illustrated in FIG. 2B. This configuration included a cylindrical permanent magnet 12 with a shaped hole at its center and four radiofrequency coils 14 arranged about the symmetry axis 16 of the magnet. The coordinate system was selected such that the symmetry axis 16 of the magnet was along the z axis. The magnet was 160 mm in diameter and 120 mm in height, and it was backed by a steel cylinder 18, 20 mm in height. The direction of the static field is marked by a block arrows in FIG. 2B.

The dimensions of each radiofrequency coil were 18.2× 13.8×2 mm, and it included 50 windings. The distance along the radial direction (perpendicular to the symmetry axis) between the center of each radiofrequency coil and the symmetry axis of the magnet was 25.1 mm. The coils engaged a plane that was 6.4 mm above the edge of the magnet, and were divided into two pairs: a first pair was situated symmetrically along the x-axis and a second pair was situated symmetrically along the y-axis. The first pair was fed by a radiofrequency source with 90° phase difference with respect to the second pair. The coils of each pair were fed with opposite phase, such that the radiofrequency fields generated by the first and second pair of coils were primarily along the x- and y-axes, respectively. This form of excitation maintained the cylindrical symmetry of the probe device.

The size of the effective volume was estimated by calculating the $^1$H NMR spectra for several cases of samples having different sizes with the goal of resolving spectral peaks with a resolution of 10 and 1 ppm. It is appreciated that the size of the effective volume depends on the spectral resolution. NMR spectra calculations were carried out by a numerical simulation of the time-domain Bloch equations. The simulation considered the specific fields' distribution at the location of the sample (one dimensional dependence) and calculated the amplitude and phase of the nutation echoes [Perlo et al., Science 308 (2005) 1279; Meriles et al., Science 293 (2001)82] for varying length of β pulses, see also FIG. 7.

The static field calculations were carried out by Maxwell 3D software (from Ansoft), and the radiofrequency fields calculations were calculated by Biot-Savart numerical integration. The magnitude of the radiofrequency field were multiplied by a constant factor so that the local gradient is as close as possible to that of the static fields (see κ in Equation 1 above).

FIGS. 3A-F show the magnetic fields of the two configurations, plotted as a function of the distance from the edge of the magnet. Static (FIG. 3A) and radiofrequency (FIG. 3B) magnetic fields of the rectangular configuration exhibited linear spatial dependence near the center of the effective volume, while the static (FIG. 3E) and radiofrequency (FIG. 3F) magnetic fields of the cylindrical configuration had quadratic field dependence. Normalized static (blue) and radiofrequency (red) fields of the rectangular (FIG. 3C) and the cylindrical (FIG. 3D) configurations are plotted in ppm (vs. center point value) vertical scale. The static field strength is also illustrated as a colored cloud in the perspective illustrations of FIGS. 2A and 2B. In the colored cloud, colors shifted to red correspond to higher field strengths and colors shifted to blue correspond to lower field strengths. Static field values in Tesla are provided on the colored scale bars shown in FIGS. 2A and 2B. In FIG. 2A the values are from $2.0933 \times 10^{-1}$ T (blue) to $2.5581 \times 10^{-1}$ T (red), and In FIG. 2A the values are from $2.0933 \times 10^{-1}$ T (blue) to $2.5581 \times 10^{-1}$ T (red), and in FIG. 2B the values are from $2.9908 \times 10^{-2}$ T (blue) to $1.6848 \times 10^{-1}$ T (red).

FIGS. 4A-H show NMR simulation results.

FIG. 4A shows the real part of the nutation echo signal as a function of the time after the β pulse for the rectangular (red) and cylindrical (green) configurations. Each point in the graph is the result of the simulation calculations for specific β pulse duration, which produces the nutation echo at the specified time of that point. Also shown is the real part of the nutation echo signal in the case of perfect linear field matching (blue), for comparison. All plots assume the existence of sample with single NMR spectral line, with negligible $T_2$ effect.

FIG. 4B shows the Fourier transform of the time domain signals shown in FIG. 4A. In the reference case, when the fields are perfectly matched, the nutation echo magnitude stays constant (with only the phase oscillating), and the corresponding spectral line (blue) has a unit magnitude. When matching is not perfect the nutation echo magnitude drops very rapidly as a function of time after the β pulse (see FIG. 4A red and green lines). This behavior is typical and in many of the calculations the simulation results showed similar time dependence, namely fast initial signal drop followed by modest long term signal decrease. This phenomenon is more pronounced as one performs the calculations for larger effective volume. It can be explained by the fact that areas in the sample where field matching is relatively poor diphase mach faster leaving after a short while only the areas with good to perfect matching to contribute to the nutation echo signal. One implication of this analysis is that in principle sample volume does not have to be confined to the effective volume since the nutation echo can serve as a spatial filtering process. In practice, as shall be shown below, unnecessary extra sample volume may increase the spectral noise and thus may degrade the spectrum quality and resolution.

Nevertheless, this unique characteristic of the nutation echo method enhances its robustness against small variations in field and probe geometry. Namely, minor changes would only lead to loss in SNR with indirect implication to spectral resolution. This is in contrast to the ex-situ shimming method in which the spectral resolution is directly affected by any probe instabilities/imperfections.

Figure 4C:
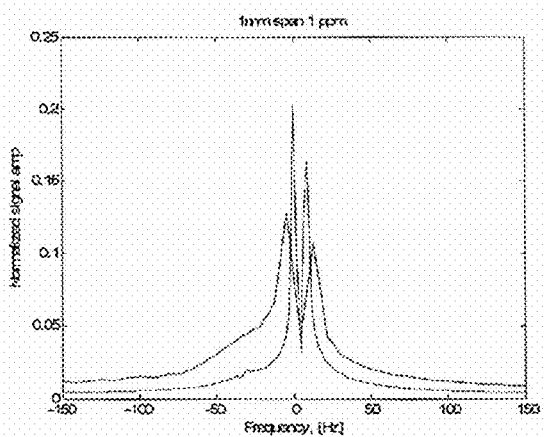
Figure 4D:
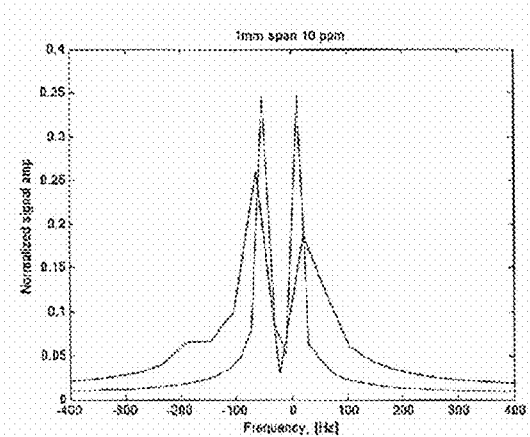
Figure 4E:
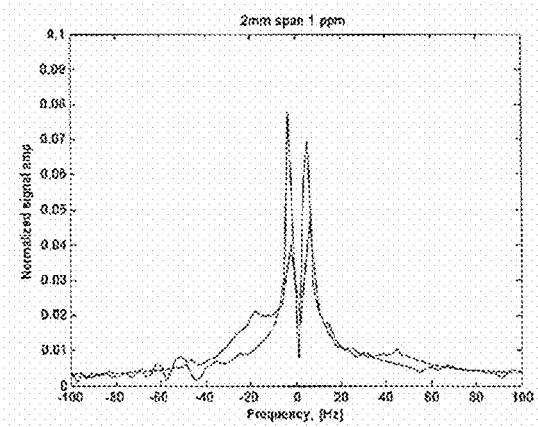
Figure 4F:
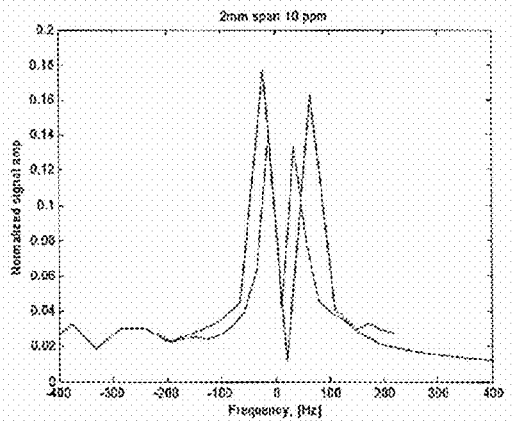
Figure 4G:
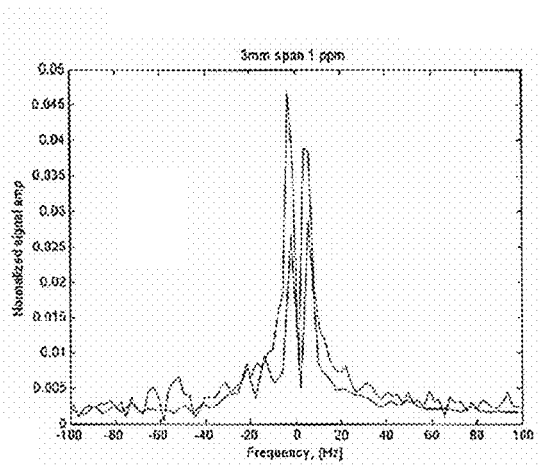
Figure 4H:
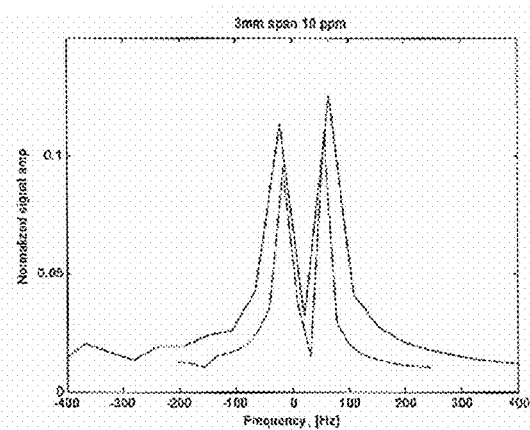

FIGS. 4C-H show NMR spectra simulations of the rectangular (red) and cylindrical (green) configurations for a one-dimensional effective volume extending over 1 mm (FIGS. 4C-D), 2 mm (FIGS. 4E-F) and 3 mm (FIGS. 4G-H), where FIGS. 4C, 4E and 4G correspond to a spectral resolution of 1 ppm and FIGS. 4D, 4F and 4H correspond to a spectral resolution of 10 ppm. As shown, for larger samples, the spectral resolution decreases. The above calculations can be used to extract various features of each of the configurations such as SNR, spectral resolution, optimal sample size and distance from the face of the probe.

Signal-to-Noise Ratio (SNR)

In NMR experiments the single shot SNR can be calculated for water sample, under ideal conditions, by the expression:

$$SNR_{SS} = \frac{9.3 \times 10^5 \cdot B_0^2 \cdot \left(\frac{B_1}{I}\right)_{RX} \cdot \Delta V}{\sqrt{4k_B \cdot BW \cdot R_{AC}}}, \quad (2)$$

where $B_0$ is the static field in Tesla, $$\left(\frac{B_1}{I}\right)_{RX}$$

is the sensitivity of the reception coil (expressed by the radiofrequency field $B_1$ generated by the coil for 1 Amp of electrical current flow), $\Delta V$ is the volume of the sample, $\kappa_B$ is Boltzmann constant, BW is the bandwidth of acquisition, and $R_{AC}$ is the radiofrequency resistance of the reception coil. Table 1 below presents the $SNR_{ss}$ for the two configurations. The calculation was based on Equation 2 with an additional loss factor of 2 to account for unavoidable instrumental limitations.

TABLE 1

| | $B_0$ [T] | $\left(\frac{B_1}{I}\right)_{RX}$ [T/A]* | BW [Hz]# | $R_{AC}$ [Ω] | $SNR_{SS}$ ($\Delta V = 1$ mm$^3$) |
|---|---|---|---|---|---|
| Rectangular | 0.23 | $1.5 \times 10^{-4}$ | 5 | 1 | 222 |
| Cylindrical | 0.13 | $2.7 \times 10^{-4}$ | 2.5 | 10 | 57 |

The SNR values in Table 1 will now be discussed in the context of the nutation echo and spectral simulations.

First consider the results for a 1 mm span. For a single spectral peak (FIG. 4B) the amplitude relative to that of the reference case is about 0.2 and about 0.4 for the rectangular and cylindrical configurations, respectively. Considering a spectrum with 2 peaks (FIG. 4C), each peak signal drops by another factor of 2, leaving only about 0.1 and about 0.2 of the total possible signal for the rectangular and cylindrical configurations, respectively. These can be accounted for during the SNR calculations. Furthermore, the spectral simulations shown in FIG. 3 assumed for simplicity one-dimensional effective volumes. For 3D volumes the normalized amplitude of the spectral peaks are the square (for the cylindrical case, which has two independent axes), or the cube (for the rectangular case) of the amplitude in the one-dimensional case (this reasoning assumes that the amount of matching that can be achieved in each independent axis is similar to that achievable in one one-dimensional calculation/optimization). Thus, for a doublet spectrum, an effective volume of 1 mm×1 mm×1 mm and a spectral resolution of 1 ppm, the $SNR_{ss}$ of Table 1 should be multiplied by a factor of about 0.001 for the rectangular configuration and about 0.04 for the cylindrical configuration. Additionally, reasonable acquisition time for ex-situ applications are expected to be of the order of 1-2 min, which implies that there can be about 100 repetitions for signal averaging. Thus, the achievable total measurement SNR in this case is about 2.2 for the rectangular configuration and about 23 for cylindrical configuration.

Figure 3A:
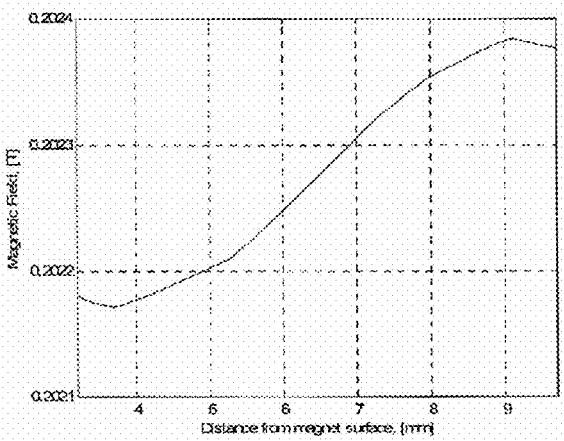
Figure 3B:
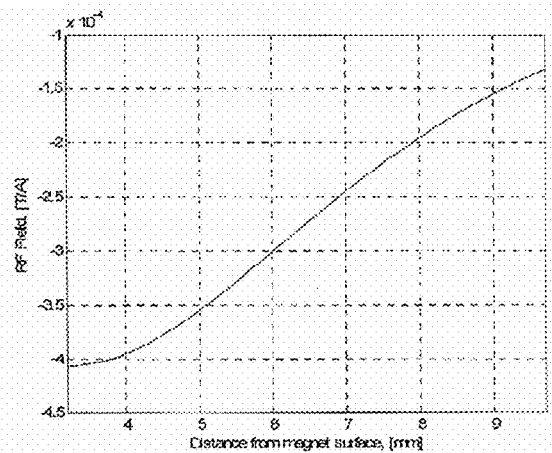
Figure 3C:
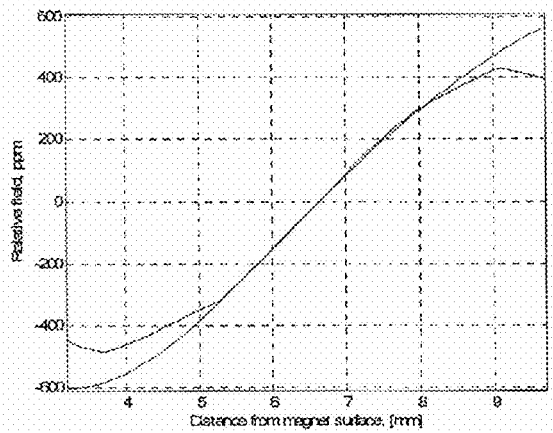
Figure 3D:
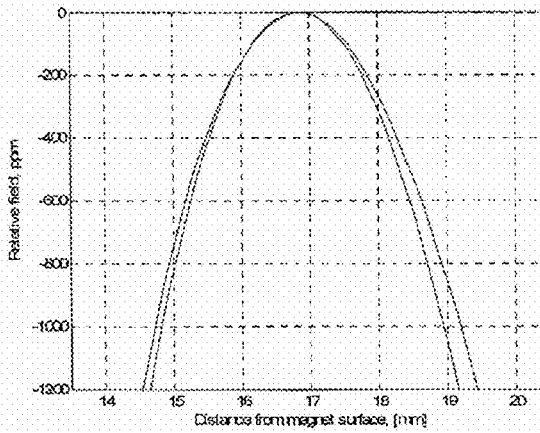
Figure 3E:
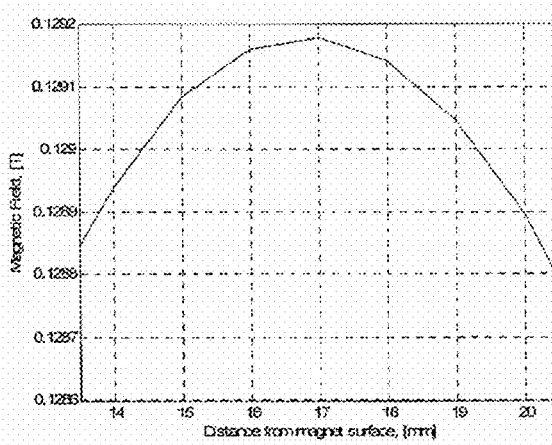
Figure 3F:
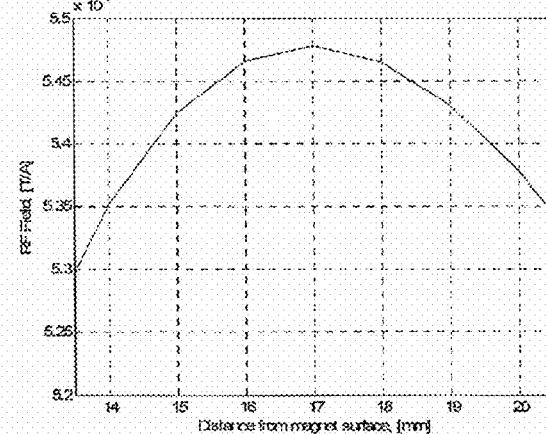

When increasing the one-dimensional span to 2 mm, the effective volume is increased by a factor of 8, but this would not necessarily result in a corresponding increase in SNR, due to a reduction in the normalized nutation echo signal (FIG. 3E). Thus, for the rectangular configuration, the normalized signal (in the one dimensional case) drops by an additional factor of about 2.4 compared to the 1 mm span case. This implies that in three dimensions the cubic dependence results in a net loss of SNR by a factor of about 1.7 (increase by a factor of 8 but reduction by a factor of about $2.4^3$=13.8). For the cylindrical case, there is a drop of signal by a factor of about 2.5, leading to net overall gain in SNR by a factor of about 1.3 (increase by a factor of 8 but reduction by a factor of about $2.5^2$=6.25).

Further increase of the one-dimensional span to 3 mm (FIG. 3G) results in a further reduction in SNR for the rectangular configuration and a small gain in SNR for the cylindrical configuration.

It is therefore concluded when spectral resolution of 1 ppm is required, the effective volumes for the rectangular and the cylindrical configurations are about 3.5 mm$^3$ and about 10 mm$^3$, respectively. The achievable NMR spectrum SNR for such volume, after 100 repetitions is about 3 for the rectangular configurations and about 30 for the cylindrical configuration.

Spectral Resolution

Reference is now made to the results of FIGS. 4D, 4F and 4H (1 ppm spectral resolution) in comparison to FIGS. 3C, 3E and 3G (10 ppm spectral resolution). As shown for a spectral resolution of 10 ppm the required collection time is much shorter and thus the normalized signal decrease is much less significant compared to the corresponding 1 ppm case. This translates to significant increase in the SNR, even after considering the larger bandwidth of noise attributed to the lower spectral resolution. For example, with a one dimensional span of 1 mm, a spectral resolution of 10 ppm and 100 repetitions, the rectangular configuration can reach a total spectral SNR of about 23, which is roughly an order of magnitude improvement relative to the 1 ppm case.

It is therefore concluded that a spectral resolution of about 1 ppm spectral resolution is beyond the reach of the rectangular configuration from the standpoint of SNR. It is further concluded that the cylindrical configuration is capable of providing a spectral resolution of about 1 ppm with an SNR of about 10.

Distance from the Probe Edge

The magnetic fields graphs demonstrate that in the cylindrical configuration, the center of the effective volume is approximately at 17 mm from the magnet. This is advantageous over the rectangular configuration in which the distance is about 6.5 mm. Note that in practice this distance is reduced by about 5 to 6.5 mm when considering the distance to the face of the probe due to the radiofrequency coils that are positioned slightly above the surface of the magnet.

Use of Superconductor Magnet

The static magnetic field unit 12 can be comprised of a superconductor magnet assembly for generating static magnetic field that has a inhomogeneity which substantially matches (e.g., within 10% or less) the inhomogeneity of the radiofrequency field. Following are calculations results for the case of a superconductor magnet assembly. The calculations were similar to the calculations above but scaled to much higher fields.

FIG. 5 is a schematic illustration of an example of a winding profile for cylindrically symmetric superconductor magnet, according to various exemplary embodiments of the present invention. In FIG. 5, blue and the red symbols represent wires carrying current in opposite directions.

FIG. 6 shows the static magnetic field (blue line) produced by the winding profile of FIG. 5 as a function of the distance from the edge of the magnet. Also shown in FIG. 6 is the static magnetic field of a permanent magnet (red line) for comparison. It is demonstrated that the winding profile shown in FIG. 5 can produce a magnetic field that is substantially the same as the magnetic field generated by the permanent magnet. It is noted that while the normalized spatial dependence of the fields are similar, the absolute magnitude achievable by the superconducting magnet can be much larger, typically from about 1 T to about 10 T larger than the magnetic field generated by the permanent magnet.

With the above reasoning, the calculated effective volume for a 300 mm diameter, 300 mm high probe device having a superconductor magnet assembly which generates a static field of 3 T at the center of the effective volume is about 1000 mm$^3$. This volume can be positioned at a distance of about 100 mm from end 22 of the probe. The spectral resolution can be from about 0.1 to about 1 ppm and a 1 min SNR for pure water sample can be about 100,000. Such properties enable the use of the probe device of the present embodiments in clinical applications with metabolites in the 1-100 mM concentration range compared to the normal water concentration of about 50M.

Additional Considerations

The required peak radiofrequency power during the β pulse is directly proportional to the field inhomogeneity of the radiofrequency coil relative to that of the static magnetic field. Consider a simple nutation echo pulse sequence, which employs a single β pulse. The length of the longest β pulse, $t_1$, required to obtain spectral resolution of $\Delta f$ is:

$$t_1 = \frac{\Delta\omega_0 \tau_1}{\Delta\omega_1} = \frac{\Delta\omega_0}{\Delta\omega_1 \Delta f}, \quad (2)$$

where $\Delta\omega_0$ and $\Delta\omega_1$ are the inhomogeneities of the static and radiofrequency fields, respectively, and $\tau_1$ is the required longest free precession time at which the nutation echo appears.

In the rectangular configuration, for example, the ratio $\Delta\omega_0/\Delta\omega_1$ is about 1, for 1 A of current flowing through the radiofrequency coil (i.e., about 1 W of peak power). For the cylindrical configuration one can get similar $\Delta\omega_0/\Delta\omega_1$ for about the same 1 W power. This implies that for a spectral resolution of 1 ppm the length of the β pulse is about 100 ms. For such a length, $T_2$ effects may become non-negligible. In some embodiments of the present invention a higher peak power amplifier is employed so as to increase $\Delta\omega_1$. In some embodiments of the present invention other nutation echo pulse sequences, such as, but not limited to, pulse sequences that involve the use of a plurality of short β pulses are employed (see e.g., Perlo et al., 2005, supra).

In some embodiments of the present invention gradient coils 26 are employed. The gradient coils 26 can be placed at or near the end 22 of device 10 which is proximal to sample 20 (see FIG. 1A). Gradient coils 26 can engage a plane which is below the plane engaged by the radiofrequency coils. Alternatively, gradient coils 26 can engage a plane which is above the plane engaged by the radiofrequency coils. Still alternatively, the gradient coils and the radiofrequency coils can engage the same plane. For example, two orthogonal pairs of coils can be arranged such that each pair is antisymmetric and creates null at a point between them on the plane. The gradient coils can also be according to the teachings of Perlo et al., "3D imaging with a single-sided sensor: an open tomography," Journal of Magnetic Resonance 166 (2004) 228, the contents of which are hereby incorporated by reference.

The use of gradient coils is particularly useful for spatial encoding and imaging of samples that extend beyond the effective volume. Nevertheless, this need not necessarily be the case since it was demonstrated above that increasing the span does not completely destroy the spectral resolution. As demonstrated above, although the normalized signal drops fast as sample span increases, the overall NMR spectral SNR does not deteriorate very fast for large samples. This is due to the spatial filtering mechanism attributed to the nutation echo which picks up the signal only from areas where the matching between the $B_0$ and the $B_1$ fields is sufficient.

Finite $T_2$ effects can become non-negligible when the static field values at the effective volume are too low. For a given $T_2$, the linewidth in Hz is $1/(\pi T_2)$, and it can be resolved by measuring the nutation echo in sufficiently long times. For a given static field $B_0$ (in Tesla units) the resolution frequency is 42.57 MHz×$B_0$. A spectral resolution of Y ppm means that, in principle, lines separated by $\Delta\nu$=42.57 MHz×$B_0$×Y/1000000 are resolvable. Finite $T_2$ effects become non-negligible if $\Delta\nu$ is lower than $1/(\pi T_2)$. For most samples of interest, $T_2$ values are in the range of 0.1-1 s, which translates to linewidth of up to about 3 Hz. This implies that static magnetic fields of about 0.1 T would be marginal for proper spectral resolution of about 1 ppm, if the measured sample has relatively short $T_2$. Thus, finite $T_2$ effects may be the limiting factor prohibiting the reduction of $B_0$ to a level that affects the spectral resolution. Finite $T_2$ effects may also reduce the distance of the effective volume from the end of the static magnetic field unit since the static magnetic field decreases away from the static magnetic field unit.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for ex situ magnetic resonance analysis, comprising:
a static magnetic field unit for generating a generally cylindrically symmetric static magnetic field outside said static magnetic field unit; and
a radiofrequency unit for generating a generally cylindrically symmetric radiofrequency field in an effective volume outside said radiofrequency unit, said radiofrequency field being perpendicular to said static magnetic field;
wherein said cylindrical symmetries are with respect to the same symmetry axis and wherein a spatial inhomogeneity of said magnetic field in said effective volume substantially matches a spatial inhomogeneity of said radiofrequency field in said effective volume.

2. The device of claim 1, being capable of providing nuclear magnetic resonance data at a spectral resolution of less than 8 ppm over an effective volume of at least 3 cubic millimeters being at a distance of at least 2 mm from an end of said static magnetic field unit.

3. The device of claim 1, being capable of providing nuclear magnetic resonance data at a spectral resolution of less than 3 ppm over an effective volume of at least 2 cubic millimeters being at a distance of at least 2 mm from an end of said static magnetic field unit.

4. The device of claim 1, being capable of providing nuclear magnetic resonance data at a spectral resolution of less than 8 ppm over an effective volume of at least 2 cubic millimeters being at a distance of at least 10 millimeters from said static magnetic field unit.

5. The device of claim 1, being capable of providing nuclear magnetic resonance data at a spectral resolution of less than 8 ppm and a signal-to-noise ratio of at least 30 for an acquisition time of about 1 min over an effective volume which is at least 2 cubic millimeters being at a distance of at least 2 millimeters from said static magnetic field unit.

6. The device of claim 1, being capable of providing nuclear magnetic resonance data at a spectral resolution of less than 3 ppm and a signal-to-noise ratio of at least 30 for an acquisition time of about 1 min over an effective volume which is at least 3 cubic millimeters being at a distance of at least 10 millimeters from said static magnetic field unit.

7. The device of claim 1, wherein said static magnetic field unit comprises a permanent magnet.

8. The device of claim 1, wherein said static magnetic field unit comprises a superconductor magnet assembly.

9. The device of claim 8, being capable of providing nuclear magnetic resonance data at a spectral resolution of less than 2 ppm over an effective volume of at least 500 cubic millimeters being at a distance of at least 20 mm from an end of said static magnetic field unit.

10. The device of claim 8, being capable of providing nuclear magnetic resonance data at a spectral resolution of less than 1 ppm over an effective volume of at least 10 cubic millimeters being at a distance of at least 20 mm from an end of said static magnetic field unit.

11. The device of claim 8, being capable of providing nuclear magnetic resonance data at a spectral resolution of less than 2 ppm over an effective volume of at least 10 cubic millimeters being at a distance of at least 50 millimeters from said static magnetic field unit.

12. The device of claim 8, being capable of providing nuclear magnetic resonance data at a spectral resolution of less than 2 ppm and a signal-to-noise ratio of at least 50,000 for an acquisition time of about 1 min over an effective volume which is at least 10 cubic millimeters being at a distance of at least 20 millimeters from said static magnetic field unit.

13. The device of claim 8, being capable of providing nuclear magnetic resonance data at a spectral resolution of less than 1 ppm and a signal-to-noise ratio of at least 50,000 for an acquisition time of about 1 min over an effective volume which is at least 50 cubic millimeters being at a distance of at least 50 millimeters from said static magnetic field unit.

14. The device of claim 1, wherein said radiofrequency unit comprises a set of radiofrequency coils arranged about said symmetry axis.

15. The device of claim 1, wherein said radio frequency unit comprises at least two sets of radiofrequency coils, and wherein different sets of radiofrequency coils are configured for different types of excitation pulses.

16. The device of claim 1, further comprising a plurality of shim coils for correcting a profile of said static magnetic field.

17. The device of claim 1, further comprising a plurality of gradient coils.

18. The device of claim 1, wherein said analysis comprises spectroscopy.

19. The device of claim 1, wherein said analysis comprises imaging.

20. The device of claim 1, wherein a spatial derivative of said magnetic field in said effective volume is proportional to a spatial derivative of said radiofrequency field in said effective volume, and wherein a coefficient κ characterizing said proportionality does not depend on the location in said effective volume or has a dependence which is less than a few tens of ppm over a range of a few millimeters in said effective volume.

21. The method of claim 1, wherein a spatial derivative of said magnetic field in said effective volume is proportional to a spatial derivative of said radiofrequency field in said effective volume, and wherein a coefficient κ characterizing said proportionality does not depend on the location in said effective volume or has a dependence which is less than a few tens of ppm over a range of a few millimeters in said effective volume.

22. A method of performing ex situ magnetic resonance analysis, comprising:
subjecting a sample to a generally cylindrically symmetric magnetic field generated outside a static magnetic field unit;
using a radiofrequency unit for applying to said sample a generally cylindrically symmetric radiofrequency field being perpendicular to said static magnetic field, wherein said sample is outside said radiofrequency unit; and
acquiring nuclear magnetic resonance data from said sample, thereby performing ex situ magnetic resonance analysis;
wherein said cylindrical symmetries are with respect to the same symmetry axis and wherein a spatial inhomogeneity of said magnetic field substantially matches a spatial inhomogeneity of said radiofrequency field.

23. The method of claim 22, wherein said acquisition of said nuclear magnetic resonance data comprises employing a nutation echo sequence.

24. The method of claim 22, wherein said application of said radiofrequency field comprises applying different types of excitation pulses using different sets of radiofrequency coils.

25. The method of claim 22, further comprising applying correcting a profile of said static magnetic field using a plurality of shim coils.

* * * * *